(12) United States Patent  
Golan

(10) Patent No.: US 11,690,637 B2  
(45) Date of Patent: Jul. 4, 2023

(54) FRACTURING CALCIFICATIONS IN HEART VALVES

(71) Applicant: Pi-Cardia Ltd., Rehovot (IL)

(72) Inventor: Erez Golan, Rehovot (IL)

(73) Assignee: Pi-Cardia Ltd., Rehovot (IL)

( * ) Notice: Subject to any disclaimer, the term of this patent is extended or adjusted under 35 U.S.C. 154(b) by 30 days.

(21) Appl. No.: 17/464,890

(22) Filed: Sep. 2, 2021

(65) Prior Publication Data

US 2021/0393281 A1 Dec. 23, 2021

Related U.S. Application Data

(63) Continuation of application No. 15/418,919, filed on Jan. 30, 2017, now abandoned, which is a continuation of application No. 13/514,090, filed as application No. PCT/US2010/055810 on Dec. 3, 2010, now Pat. No. 9,554,816.

(60) Provisional application No. 61/267,029, filed on Dec. 5, 2009, provisional application No. 61/356,617, filed on Jun. 20, 2010.

(51) Int. Cl.
  *A61B 17/22* (2006.01)
  *A61B 17/221* (2006.01)
  *A61B 90/00* (2016.01)
  *A61B 17/00* (2006.01)

(52) U.S. Cl.
  CPC ........ *A61B 17/22031* (2013.01); *A61B 17/22* (2013.01); *A61B 17/221* (2013.01); *A61B 17/22012* (2013.01); *A61B 2017/00544* (2013.01); *A61B 2017/22069* (2013.01); *A61B 2017/22098* (2013.01); *A61B 2090/064* (2016.02)

(58) Field of Classification Search
  CPC ........ A61B 17/12027; A61B 17/12122; A61B 17/12168; A61B 17/22031; A61B 17/3207; A61B 17/32075; A61B 2017/22098
  See application file for complete search history.

(56) References Cited

U.S. PATENT DOCUMENTS

| | | | |
|---|---|---|---|
| 8,382,796 B2* | 2/2013 | Blaeser | A61B 17/0057 606/213 |
| 2005/0075662 A1* | 4/2005 | Pedersen | A61M 25/10 977/875 |
| 2006/0100553 A1* | 5/2006 | Lodin | A61B 17/2202 606/34 |
| 2006/0229659 A1* | 10/2006 | Gifford | A61F 2/2445 606/200 |
| 2012/0116289 A1* | 5/2012 | Hawkins | A61B 17/22012 606/200 |

* cited by examiner

*Primary Examiner* — Sarah W Aleman
(74) *Attorney, Agent, or Firm* — Dekel Patent Ltd.; David Klein

(57) ABSTRACT

A device for fracturing calcifications in heart valves including an expandable stabilizer and expandable impactor arms assembled on and deployed by a delivery system, wherein the delivery system is operable to move the impactor arms, while in an expanded position, with respect to the stabilizer with sufficient energy so as to fracture a calcification located in tissue which is sandwiched between the stabilizer and the impactor arms.

15 Claims, 21 Drawing Sheets

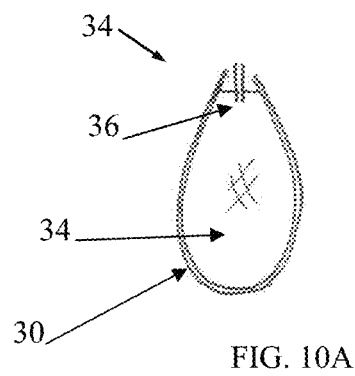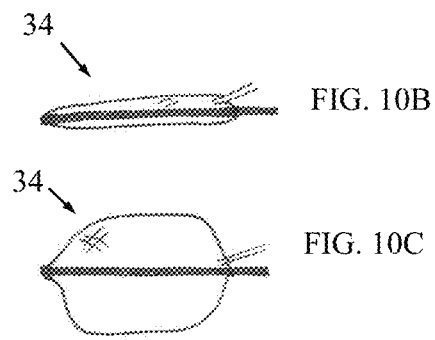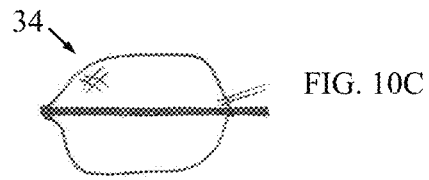
FIG. 10A
FIG. 10B
FIG. 10C
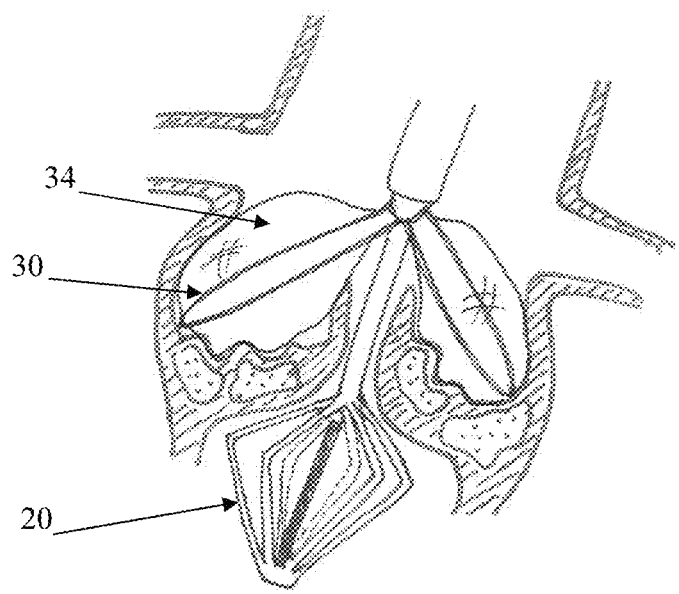
FIG. 11

FRACTURING CALCIFICATIONS IN HEART VALVES

FIELD OF THE INVENTION

The present invention generally relates to devices and methods for fracturing calcifications in heart valves, such as aortic valve leaflets.

BACKGROUND OF THE INVENTION

Essential to normal heart function are four heart valves, which allow blood to pass through the four chambers of the heart in the proper flow directions. The valves have either two or three cusps, flaps, or leaflets, which comprise fibrous tissue that attaches to the walls of the heart. The cusps open when the blood flow is flowing correctly and then close to form a tight seal to prevent backflow.

The four chambers are known as the right and left atria (upper chambers) and right and left ventricles (lower chambers). The four valves that control blood flow are known as the tricuspid, mitral, pulmonary, and aortic valves. In a normally functioning heart, the tricuspid valve allows one-way flow of deoxygenated blood from the right upper chamber (right atrium) to the right lower chamber (right ventricle). When the right ventricle contracts, the pulmonary valve allows blood to flow from the right ventricle to the pulmonary artery, which carries the deoxygenated blood to the lungs. The mitral valve, allows oxygenated blood, which has returned to the left upper chamber (left atrium), to flow to the left lower chamber (left ventricle). When the left ventricle contracts, the oxygenated blood is pumped through the aortic valve to the aorta.

Certain heart abnormalities result from heart valve defects, such as is stenosis or calcification. This involves calcium buildup in the valve which impedes proper valve leaflet movement.

SUMMARY OF THE INVENTION

The present invention seeks to provide improved devices and methods that may be used for fracturing calcifications in aortic valve leaflets, in order to increase leaflet pliability and mobility, either as stand alone treatment, bridge treatment or preparation of the "landing zone" for trans-catheter valve implantation.

The term "fracture" refers to any kind of reduction in size or any modification in shape or form, such as but not limited to, fracturing, pulverizing, breaking, grinding, chopping and the like.

There is provided in accordance with an embodiment of the invention a device for fracturing calcifications in heart valves including a catheter including an external shaft in which are disposed an expandable stabilizer, an impactor shaft on which are mounted expandable impactor arms, and an internal shaft, characterised in that the internal shaft is movable to cause the impactor arms to expand outwards and be locked in an expanded shape, and wherein an impacting element is movable to cause the impactor arms, while in the expanded shape, to move towards the tissue with sufficient energy so as to fracture a calcification located in tissue which is fixed by the stabilizer in a certain position vis-à-vis the impactor arms.

In accordance with a non-limiting embodiment of the invention the impacting element includes the internal shaft which is connected to a distal portion of the impactor arms and which is operative to move relative to the impactor shaft to expand the impactor arms outwards and to cause the impactor arms, while in the expanded shape, to move towards the stabilizer with the sufficient energy. The internal shaft may be lockable relative to the impactor shaft so that the impactor arms are fixed.

In accordance with a non-limiting embodiment of the invention the impacting element includes a weight and a biasing device, wherein the biasing device urges the weight towards the impactor arms with the sufficient energy. In one example, the weight is mounted on the biasing device which is fixed to a distal tip of the catheter. In another example, the weight is fixed to the internal shaft of the catheter. In yet another example, the biasing device includes a pneumatic energy source connected to a pressurized air source.

In accordance with a non-limiting embodiment of the invention the stabilizer includes a stabilizer structure that includes one or more elements (of any form or shape, such as rods, loops or more complex structures) optionally covered by a stabilizer cover. The stabilizer may include a stabilizer structure covered by a covering balloon. An inflate/deflate tube may be inserted into the covering balloon. A first pressure sensor may be located near the stabilizer (in the portion of the catheter that lies in the aorta) and a second pressure sensor may be located near the impactor arms (in the portion of the catheter that lies in the LVOT or left ventricle). The device can be designed in a "reverse" manner for trans-apical use, so that the impactor is proximal and the stabilizer may be positioned at a distal tip of the device. Stabilizer arms may be expandable outwards from the external shaft.

BRIEF DESCRIPTION OF THE DRAWINGS

The present invention will be understood and appreciated more fully from the following detailed description, taken in conjunction with the drawings in which:

FIGS. 7-10C are simplified illustrations of several types of stabilizers, in accordance with different non-limiting embodiments of the present invention, which can be used to effectively position the distal portion of the device, hold a portion of the leaflets in place during impact and to counteract the impact applied to the ventricular aspect of the valve leaflets.

FIG. 11 is a simplified illustration of impactor arms having more than one arm facing each leaflet, in accordance with a non-limiting embodiment of the present invention.

DETAILED DESCRIPTION OF EMBODIMENTS

Figure 1:
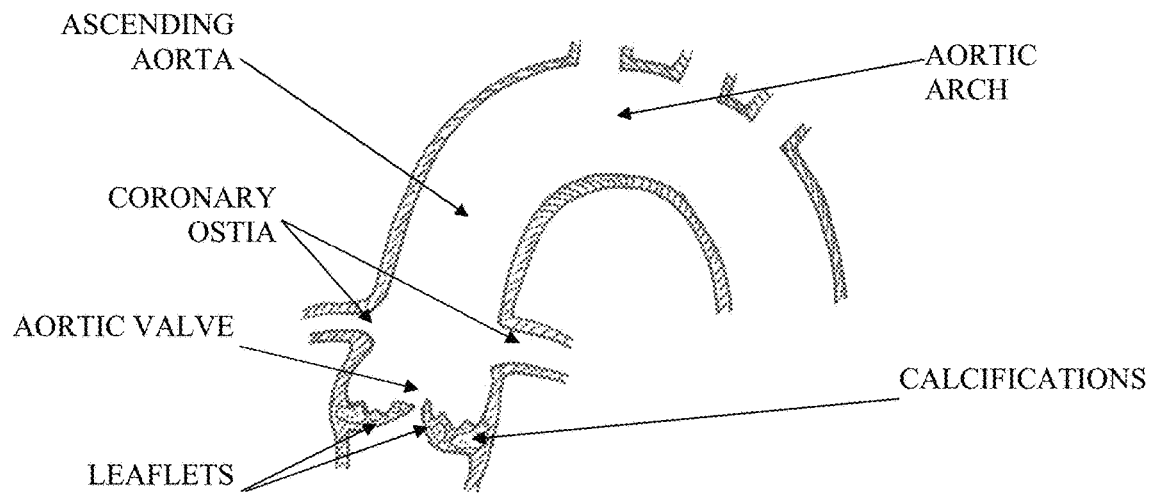
FIG. 1 is a simplified illustration of the anatomy of a calcified aortic valve, ascending aorta and aortic arch.

Reference is now made to FIG. 1, which illustrates the anatomy of a calcified aortic valve, ascending aorta and aortic arch. Calcifications may be embedded in the valve leaflets, which are connected to the aortic wall just below the coronary ostia.

Figure 2:
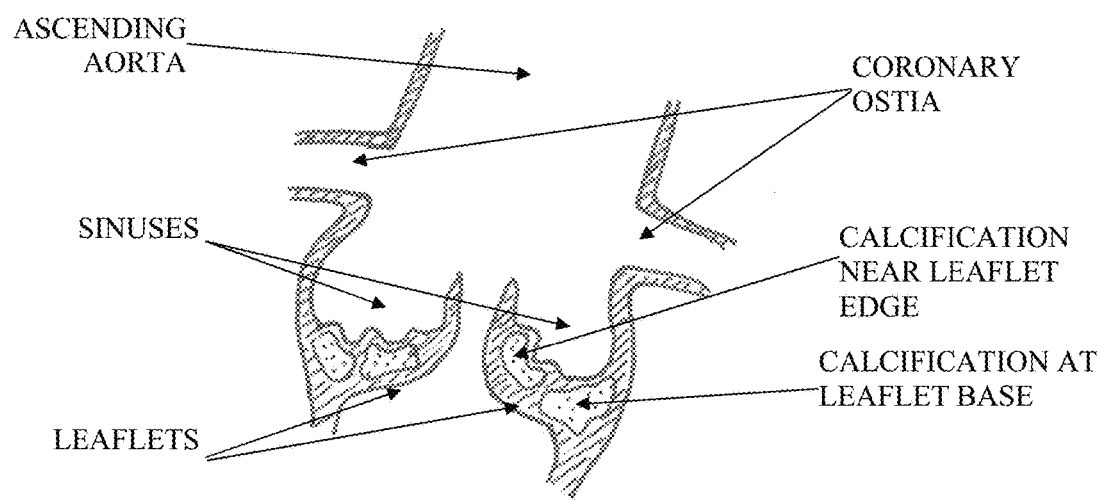
FIG. 2 is an enlarged view of a calcified aortic valve.

Reference is now made to FIG. 2, which is an enlarged view of a calcified aortic valve. The leaflets create concave sinuses on their aortic aspect, just below the coronary ostia. Calcification can be embedded in the leaflets, making the leaflets thicker and less pliable. Specifically, calcification that occurs at the leaflet base, i.e., where the leaflet connects to the annulus or aortic wall, can significantly impair the mobility of the leaflet, similar to friction in a door-hinge.

Figure 3:
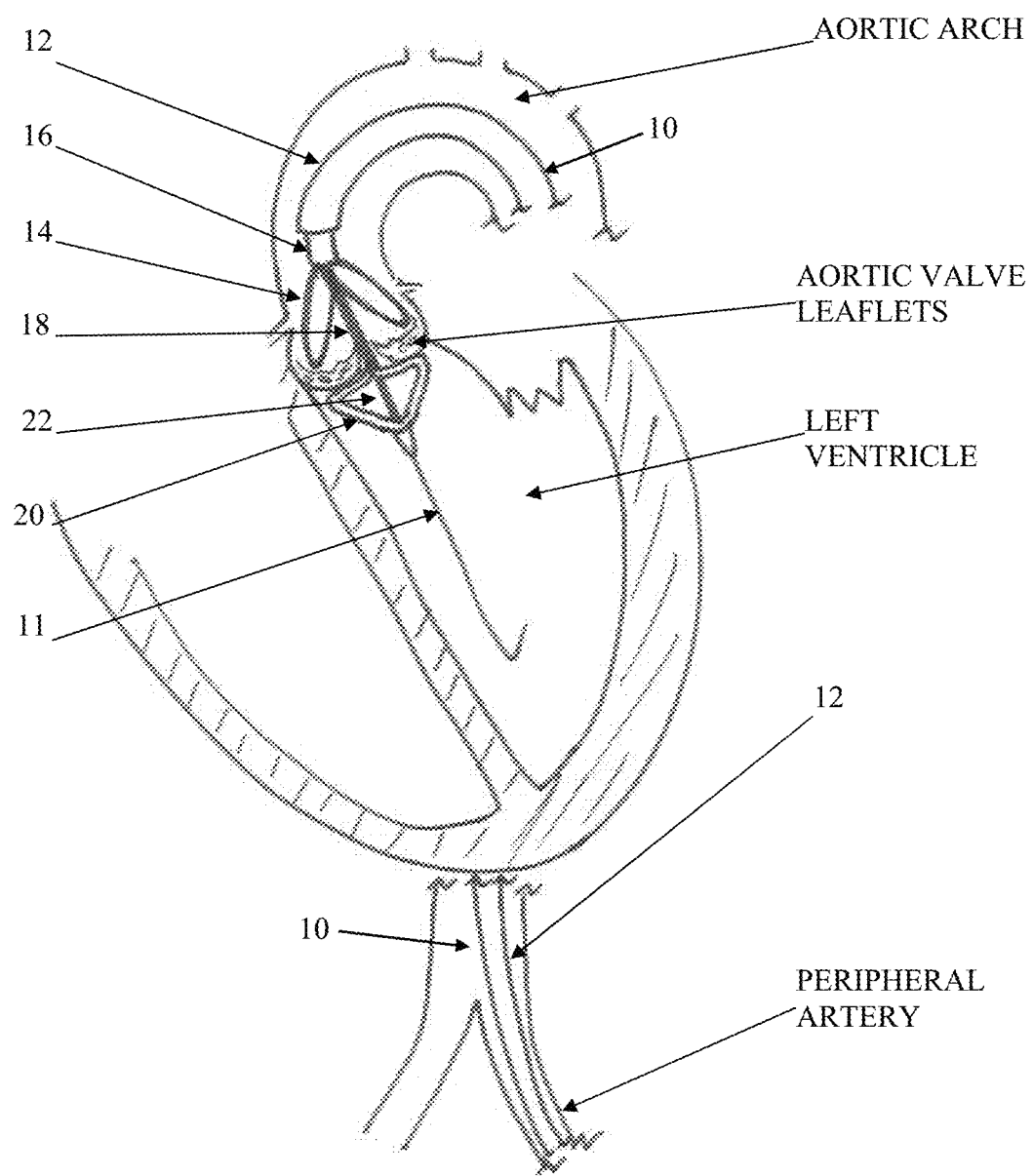
FIG. 3 is a simplified illustration of a distal part of an impactor catheter system that can be used for fracturing aortic valve calcifications, constructed and operative in accordance with a non-limiting embodiment of the invention.

Reference is now made to FIG. 3, which illustrates a distal part of an impactor catheter system that can be used for fracturing aortic valve calcifications, constructed and operative in accordance with a non-limiting embodiment of the invention.

A catheter 10 may be delivered over a guide-wire 11 through a vessel, such as the peripheral artery, using a retrograde approach, through the aortic arch and into the ascending aorta, just above the aortic valve. At this stage, all catheter components are still covered by a catheter external shaft 12. The external shaft 12 is then retracted so that an expandable (e.g., self-expanding) stabilizer 14, connected to a stabilizer shaft 16, opens up. Stabilizer 14 is used to guide, position and anchor the catheter distal part in the sinuses, just above the valve leaflets. It is noted that catheter 10 is just one example of a delivery system used to deliver and manipulate a stabilizer and impactor arms described below to impact calcifications. Optionally, the stabilizer and impactor arms described below may be delivered and/or manipulated by other devices other than a catheter, such as a guidewire or system of guidewires and push/pull wires.

An impactor shaft 18, including impactor arms 20, is then pushed forward (distally) through the center of the valve into the left ventricle. When pushed forward the impactor arms 20 are folded so that they can easily cross the valve. An internal shaft 22, which is connected to the distal portion of the impactor arms 20, is then pulled proximally to cause the impactor arms 20 to open (expand) outwards sideways and lock them in the expanded shape. Impactor and internal shafts 18 and 22 are then pulled back (proximally) a bit in order for the impactor arms 20 to make good contact with the ventricular aspect of the leaflets, so that the leaflets are "sandwiched" between the proximally-located stabilizer 14 (from above in the sense of the drawing) and the distally-located impactor arms 20 (from below in the sense of the drawing). In order to fracture leaflet calcifications, impactor arms 20 are pulled abruptly towards the leaflet tissue, while the stabilizer 14 holds the relevant portion of the leaflets in place, by pulling impactor and internal shafts 18 and 22 at a speed of at least 1 m/sec, such as without limitation, around 5-20 m/sec, but with an amplitude of at least 0.5 mm, such as without limitation, about 0.5-3 mm, so that calcification is fractured but soft tissue is unharmed.

Figure 4:
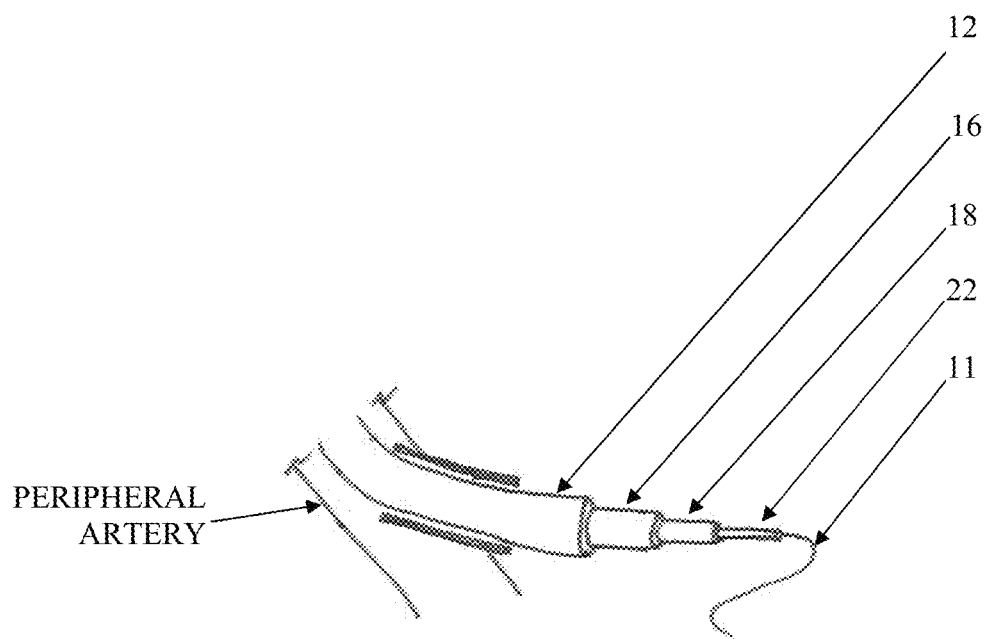
FIG. 4 is a simplified illustration of several shafts that come out at the proximal side of the catheter of FIG. 3.

Reference is now made to FIG. 4, which illustrates the several shafts that come out at the proximal side of the catheter 10 shown in FIG. 3. The entire manipulation of catheter 10 is done by controlling the relative positions of these shafts. For example, as shown in FIG. 3, the internal shaft 22 is pulled relative to impactor shaft 18 in order to open up impactor arms 20. The internal shaft 22 and the impactor shaft 18 are locked together so that the impactor arms 20 are fixed. For effective impact to be produced at the distal portion of the catheter, the internal/impactor shafts 22/18 are pulled together abruptly relative to the valve leaflet tissue while stabilizer shaft 16 is fixed. The abrupt pull at the proximal side is conveyed to the distal part.

Figures 5, 5A, 5B:
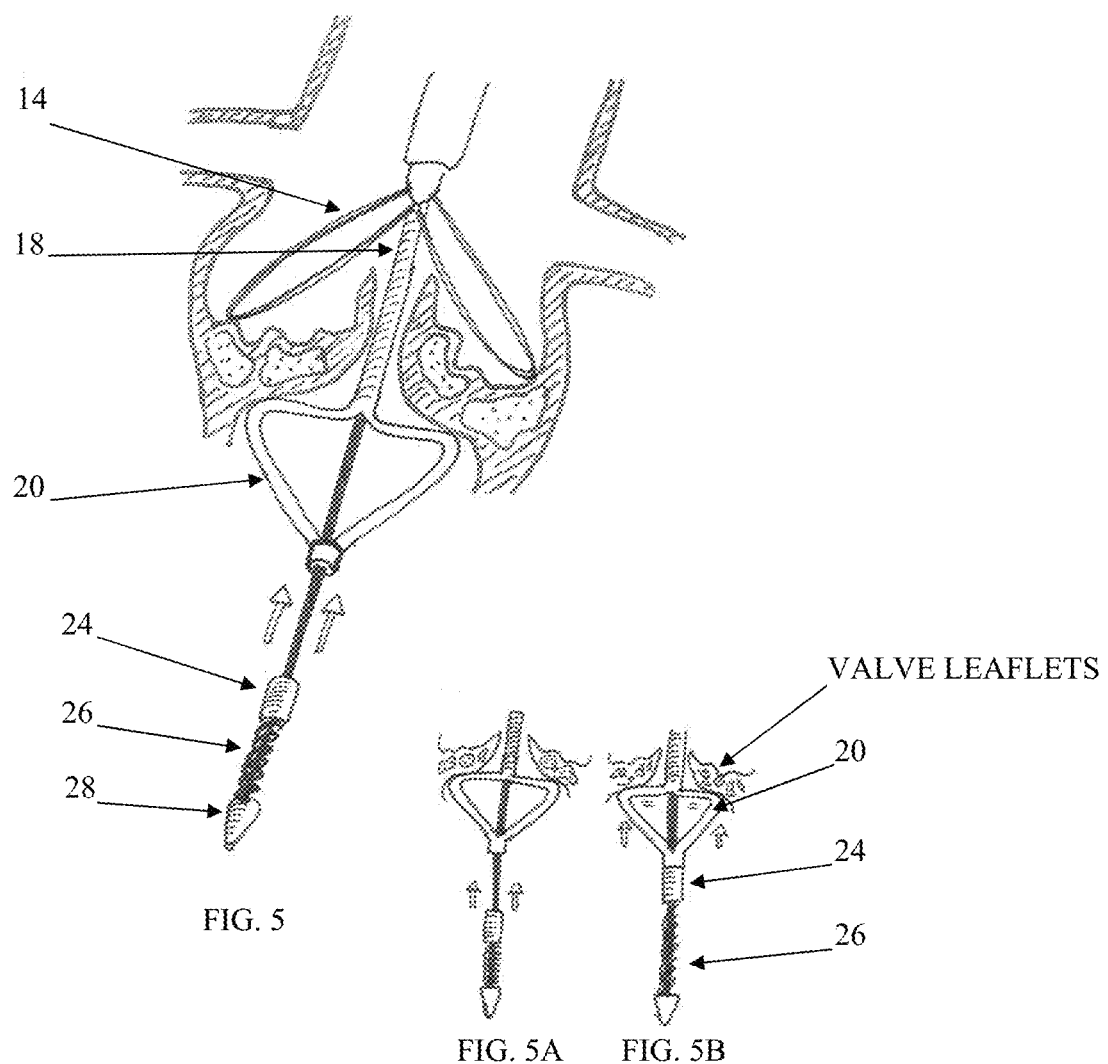
FIG. 5 is a simplified illustration of a device for fracturing calcifications in heart valves, in accordance with another non-limiting embodiment of the present invention, employing a weight.
FIGS. 5A and 5B are simplified illustrations of the weight before and after impact, respectively.
Figures 6, 6A:
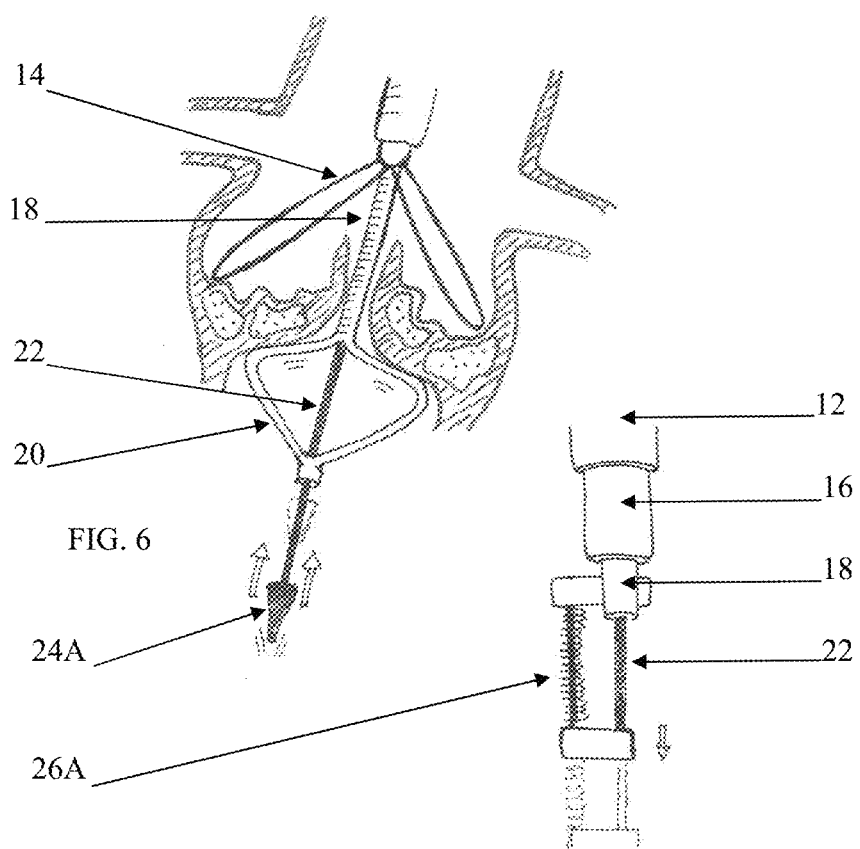
FIGS. 6 and 6A are simplified illustrations of a device for fracturing calcifications in heart valves with a weight, in accordance with yet another non-limiting embodiment of the present invention.

Reference is now made to FIG. 5, which illustrates an alternative mechanism for generating impact at the distal part of the catheter. A weight 24 is mounted on a biasing device 26 (e.g., a coil spring) that is fixed to a distal tip 28 of the catheter. Before impact (FIG. 5A), weight 24 is pushed towards distal tip 28 so that biasing device 26 is contracted. In order to generate impact, weight 24 is released so that biasing device 26 is allowed to accelerate the weight 24 until it hits the impactor arms 20 (FIG. 5B). The impactor arms 20 in turn impact the calcified leaflets. In order to maximize the impact velocity of the impactor arms 20 given a certain momentum of the accelerated weight 24, the mass of the impactor arms 20 may be diminished. This can be partly achieved by selecting an impactor shaft 18 that is also spring-like, minimizing the pushability of the impactor shaft 18, or by making the impactor arms 20 "floating" and free to move with no friction with respect to the other parts of the catheter during impact Reference is now made to FIG. 6, which illustrates yet another alternative mechanism for generating impact at the distal portion of the catheter. A weight 24A (can be the catheter tip) is fixed to the internal shaft 22 of the catheter (in this configuration the impactor arms 20 are not connected to the internal shaft 22). Before impact the internal shaft 22 is pushed distally so that the weight 24A moves a certain distance (can be a few mm to several centimeters) away from the impactor arms 20. In order to generate impact, the weight 24A is now accelerated proximally until it hits the impactor arms 20 with high velocity. A biasing device 26A (one version of which is illustrated in FIG. 6A), a pneumatic mechanism, or any other mechanism can be used in order to generate the required acceleration of the mass. The advantage of this method over the method described in FIGS. 3-4 is that when the energy source is external, it may be easier to generate high velocities at the distal portion of the catheter by using more powerful biasing devices or energy sources.

Reference is now made to FIGS. 7-10, which illustrate several types of stabilizers, which can be used to effectively position the distal portion of the catheter relative to the valve anatomy, hold certain portions of the valve leaflets in place during impact and also counteract the impact applied to the ventricular aspect of the valve leaflets. Ideally one would like to maximize the counteract force on the aortic aspect of the leaflets during impact while making sure the stabilizer surface is sufficiently compliant and blunt so to minimize injury to the leaflet surface.

Figure 7:
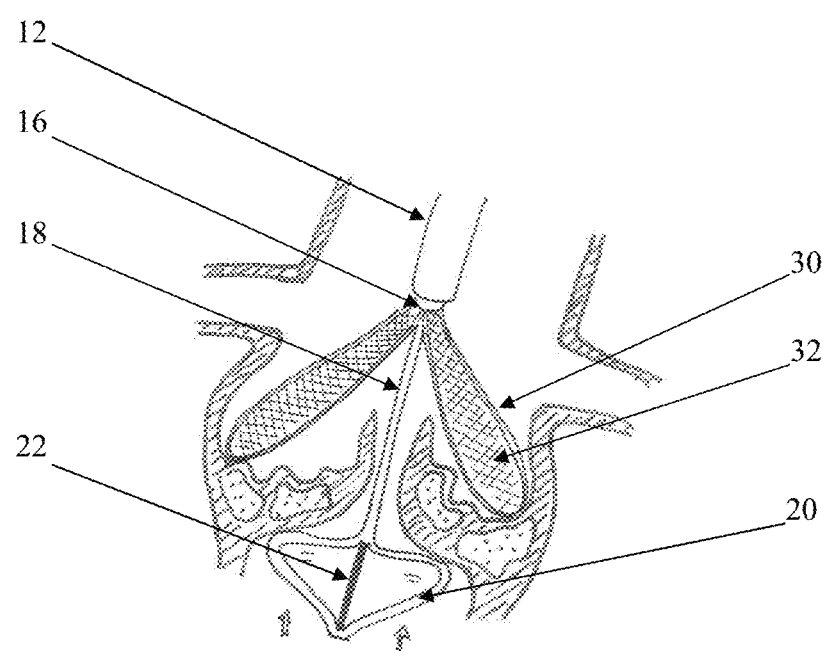

Reference is now made to FIG. 7, which illustrates an stabilizer structure 30 that can take the form of one or more loops (e.g., at least one loop fits into each of the sinuses above the leaflets, two or more for bicuspid aortic valves and three or more for tricuspid aortic valves). The stabilizer structure 30 is (optionally) covered by a stabilizer cover 32, which can be a thin metal mesh (net), a solid plastic surface, etc. If the stabilizer cover 32 is solid, or if it is based on a net with pores that are small enough, then the stabilizer cover 32 can be used as an embolic protection means, i.e., at the end of the impact procedure, if any emboli have been generated, then they can be safely collected into the catheter when folding back the stabilizer using the external shaft.

Figure 8:
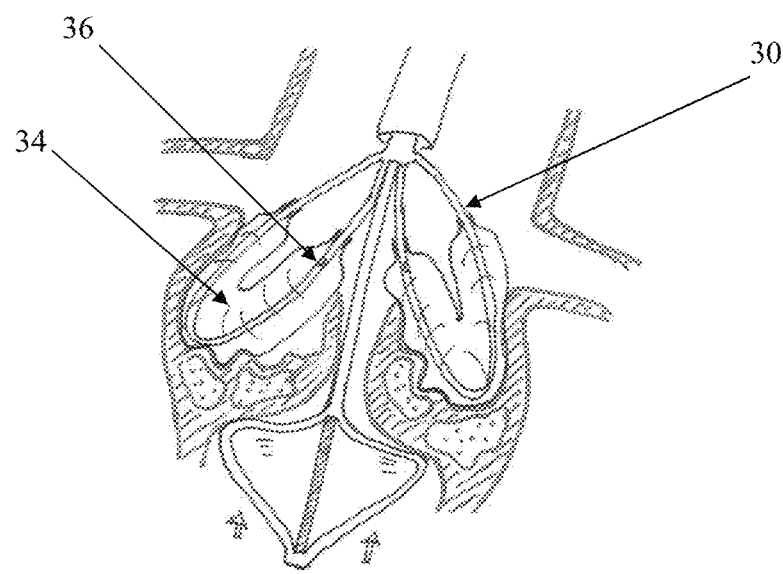

Reference is now made to FIG. 8, which illustrates an alternative stabilizer design, which incorporates a covering balloon 34 on each stabilizer structure 30. Each balloon 34 is elongated and its central axis follows the curvature of the loops that make up the stabilizer structure 30. The loops can also be used as inflate/deflate tubes for the balloons, with fluid for the inflation passing through one or more inflation/deflation openings 36. The great advantage of the balloon-based stabilizer is that the stabilizer can be positioned in the sinuses with the balloons deflated. Then the balloons 34 can be inflated to generate full contact with the leaflets surface, maximizing the impact counteract force, while avoiding injury.

Figure 9:
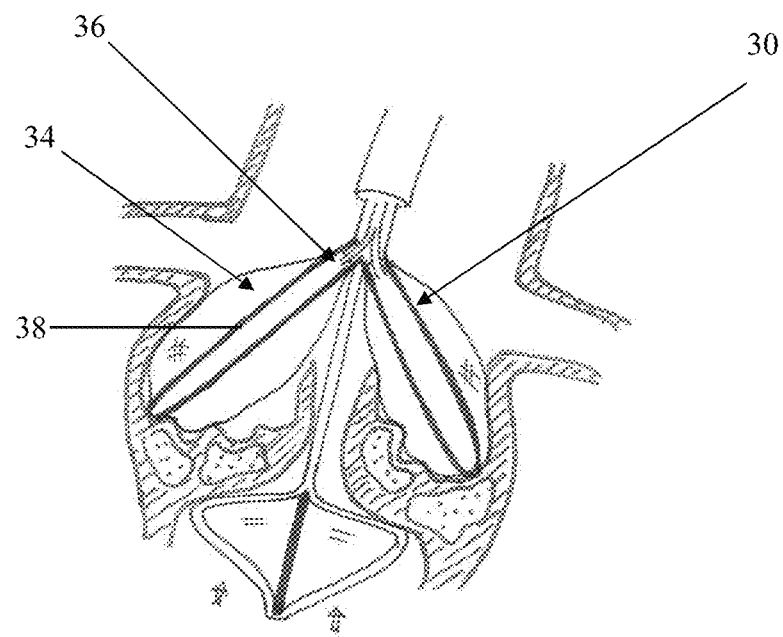

Reference is now made to FIG. 9, which illustrates yet another design of a balloon-based stabilizer. Each of the three covering balloons 34 covers one of the stabilizer structure loops 30. An inflate/deflate tube 38 can be inserted into each balloon on its proximal side. FIG. 10A illustrates balloon 34 as viewed from above. FIGS. 10B and 10C illustrate balloon 34 from the side, respectively deflated and inflated.

Reference is now made to FIG. 11, which illustrates another configuration of impactor arms 20, which comprises more than one arm facing each leaflet. It may be readily understood that the number and geometry of the impactor arms are based on the optimal locations where one wishes to impact the leaflets, e.g., number and orientation of impact lines, points or regions per leaflet, impact closer to leaflet base or tip, etc.

Figure 12:
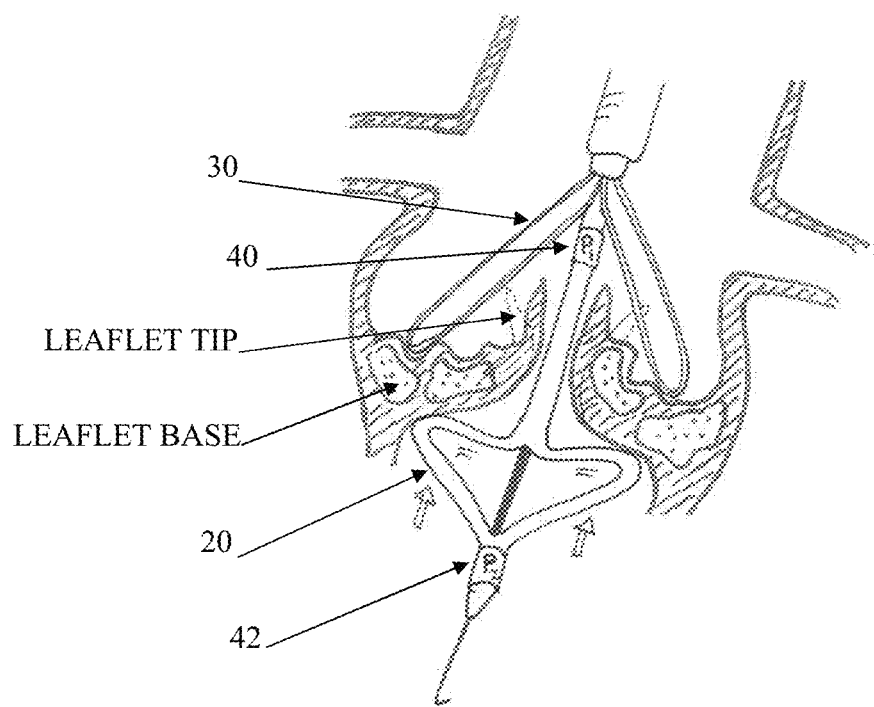
FIG. 12 is a simplified illustration of an impactor catheter, in accordance with a non-limiting embodiment of the present invention, which optimally maintains valve function during the procedure while allowing continuous measurement of the blood pressure gradient between the left ventricle and the aorta.

Reference is now made to FIG. 12, which illustrates a configuration of the impactor catheter, which optimally maintains valve function during the procedure while allowing continuous measurement of the blood pressure gradient between the left ventricle and the aorta. The impactor arms 20 and stabilizer structure 30 contact the leaflets only at their bases, i.e. near the annulus, where heavily calcified leaflets are typically immobile. The leaflet tips remain free to move, so that overall valve function is almost undisturbed by the device when it delivers impact. Two pressure sensors, a first pressure sensor 40 above the valve (near the stabilizer) and a second pressure sensor 42 below the valve (near the impactor arms) measure the aortic and ventricular blood pressures, respectively. This allows continuous measurement of the pressure gradient across the valve, which can be used as a very important real time feedback for the success of the procedure. Alternatively to incorporating pressure sensors in the device, one can design sufficiently large conduits in the catheter having a distal opening at each region of interest where pressure needs to be measured and a proximal port that can be connected to a pressure sensor outside the patient body.

Figure 13:
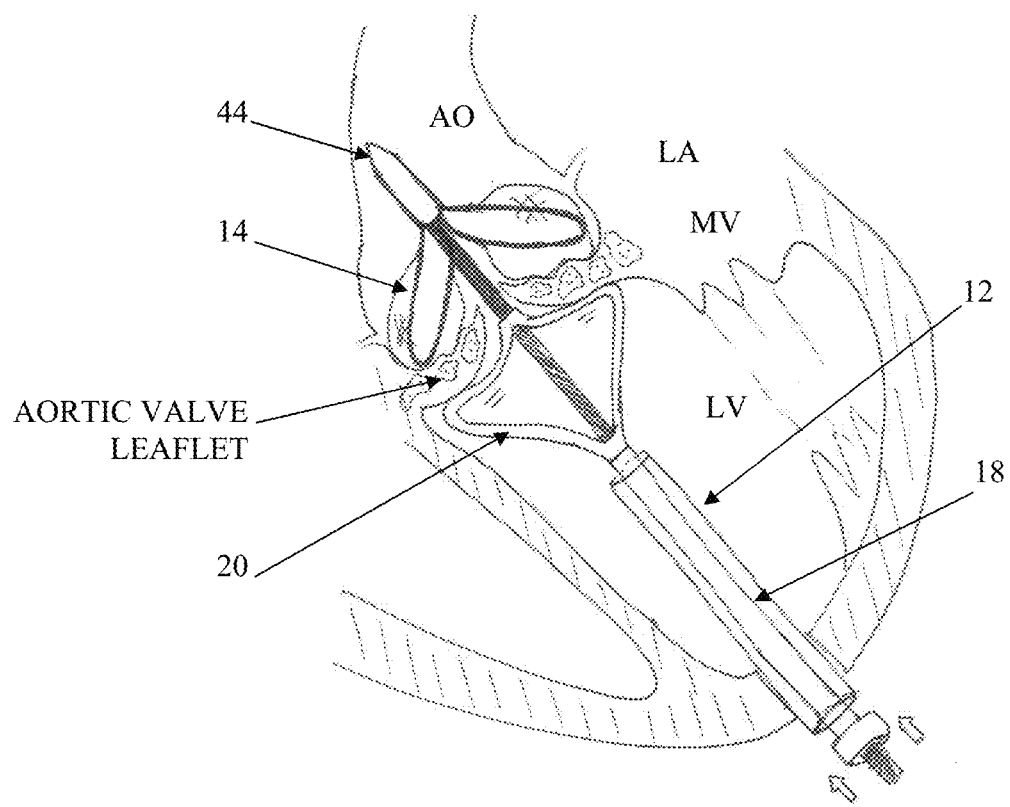
FIG. 13 is a simplified illustration of a trans-apical configuration of a device that delivers impact to the calcified valve leaflets, in accordance with a non-limiting embodiment of the invention.

Reference is now made to FIG. 13, which illustrates a trans-apical configuration of a device that delivers impact to the calcified valve leaflets. Similar elements are similarly designated as above. The trans-apical approach, while being more invasive than the trans-femoral approach, allows the device to be rigid and short, thereby potentially improving the delivery of impact from the proximal (external) portion of the device to the impactor arms on its distal portion. The stabilizer 14 is positioned closer to the distal tip 44 of the device. The tip 44 must first cross the valve and open the stabilizer 14 to position the device, hold certain portions of the leaflets and counteract the impact.

Figure 14:
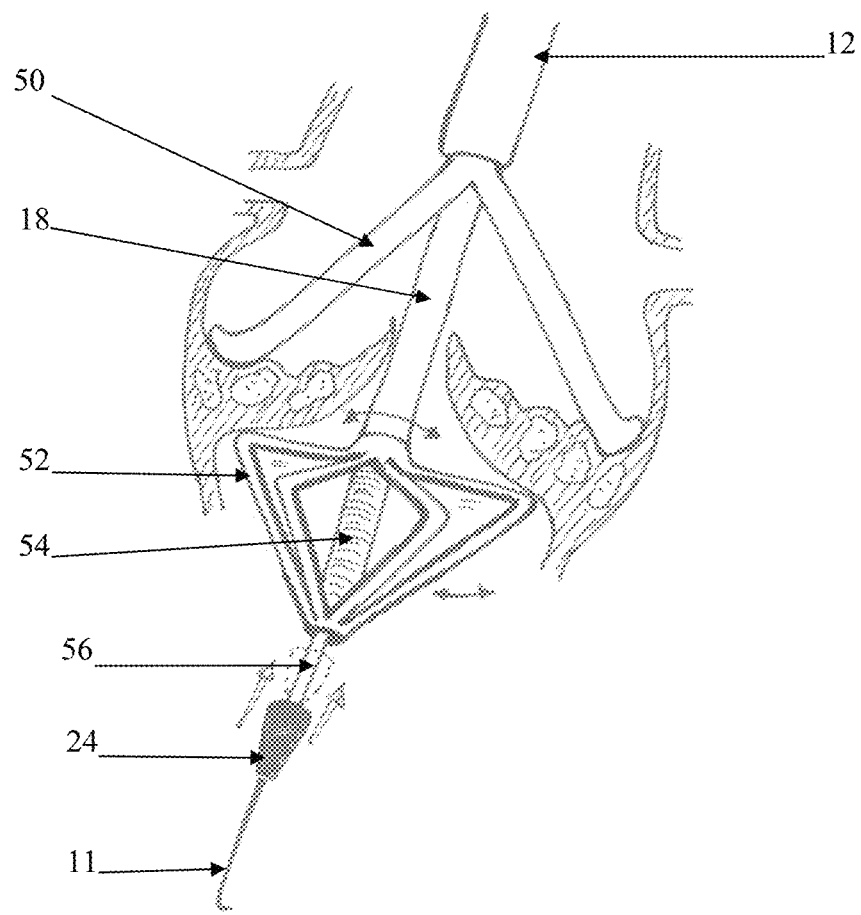
FIG. 14 and FIG. 15 are simplified illustrations of an impactor catheter based on a pneumatic energy source on the proximal side of the catheter and a weight-pull impact mechanism on the distal portion, in accordance with a non-limiting embodiment of the invention.
Figure 15:
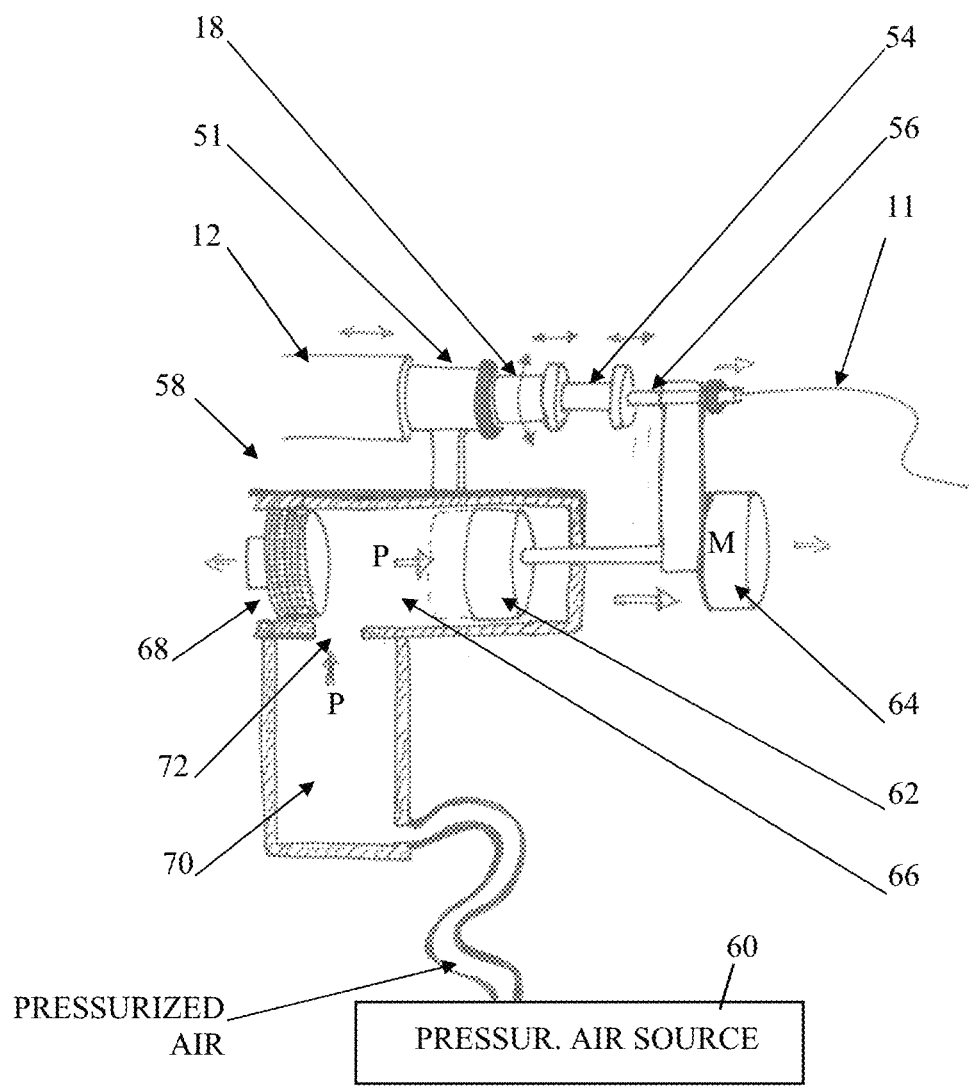

Reference is now made to FIG. 14 and FIG. 15, which illustrate an embodiment of an impactor catheter based on a pneumatic energy source on the proximal side of the catheter and a weight-pull impact mechanism on the distal portion. Again, similar elements are similarly designated as above.

Reference is now made to FIG. 14, which illustrates the distal end of the catheter. The catheter is delivered over guide wire 11 into the valve. The external sheath (shaft) 12 is retracted to expose stabilizer arms 50 which expand outwards from external shaft 12. (Stabilizer arms 50 extend from a stabilizer shaft 51 shown in FIG. 15.) The catheter is then pushed distally until stabilizer arms 50 make sufficient contact with the aortic aspect of the valve leaflets. The impactor is then advanced through the center of the valve (over guide wire 11) into the LVOT (Left Ventricular Outflow Tract).

This embodiment includes impactor arms 52, which are preferably, but not necessarily, cut out of a nitinol tube and are pre-shaped to be normally half-open. The distal ends (or one common distal end) of the impactor arms 52 are/is fixed (e.g., welded) to an internal tube (shaft) 54 which is free to move back and forth inside the impactor tube (shaft) 18. When the internal tube 54 is pulled proximally by the operator on the proximal side of the catheter, the impactor arms 52 extend outwards sideways, increasing the impactor diameter. When the internal tube 54 is pushed distally, the impactor arms 52 close or decrease their diameter. Varying the relative position of the internal tube 54 relative to impactor shaft 18 allows the operator to set the optimal impactor diameter per treated valve during the procedure. Furthermore, it allows the operator to select the regions on the calcified leaflets, which are impacted. Another option shown in this embodiment is the capability to rotate the impactor vis-à-vis the stabilizer (or together with the stabilizer) and the valve leaflets, in order to impact yet additional (or different) regions on the valve leaflets. Upon setting the impactor arms diameter and angular position, these settings can be now locked by the user (by locking the position of the internal tube 54 at the control side of the catheter in the hands of the operator). The impactor is now pulled gently until it makes sufficient contact with the ventricular side of the leaflets and is now locked in longitudinal position as well.

Weight 24 can be pulled proximally as described above by means of a weight pull shaft 56.

Reference is now made to FIG. 15, which illustrates the proximal side of the impactor catheter described in FIG. 14. A pneumatic energy source 58 (which serves as the biasing device) is connected to a pressurized air source 60 (operating room wall inlet, compressor, balloon etc.). The body of the pneumatic energy source 58 is preferably connected to the stabilizer shaft 51, in order to counteract the impact applied to the valve leaflets on the distal portion of the catheter. The longitudinal position of the internal shaft 54 with respect to the impactor shaft 18, as well as the longitudinal and angular position of the impactor shaft 18, are set and locked by the user as described in FIG. 14. The weight/pull shaft 56 is now pushed to the most distal position and then connected to a piston 62 and proximal mass 64. Piston 62 is arranged to slide in a main cylinder 66, which houses a pneumatic valve 68 and which is open to air flow from an air container 70 via an air inlet 72. When pneumatic valve 68 is opened by the operator, the pressurized air in air container 70 is released through air inlet 72 into main cylinder 66, thereby accelerating piston 62 and proximal mass 64 rapidly over a certain distance. Piston 62 and proximal mass 64 gain relatively high energy (momentum) while pulling the weight/pull shaft 56 that are connected to the distal weight 24 at the tip of the catheter. Upon reaching a certain travel distance, the distal weight 24 hits the impactor arms 52, which then transfers the energy to the valve calcification to produce fractures. Using the weight/pull mechanism allows to transfer high impact energy over a flexible catheter.

Figure 16A:
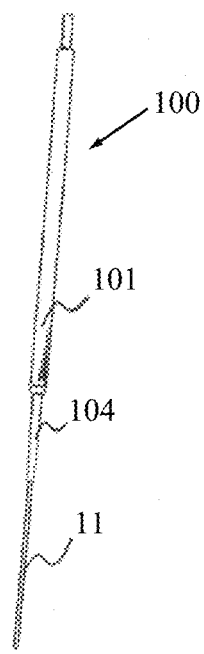
FIGS. 16A-16D are simplified illustrations of an impactor device, constructed and operative in accordance with another non-limiting embodiment of the present invention.
Figure 16B:
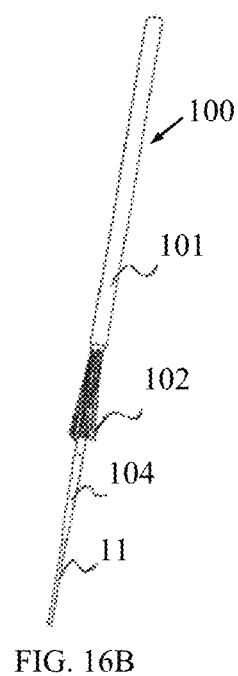
Figure 16C:
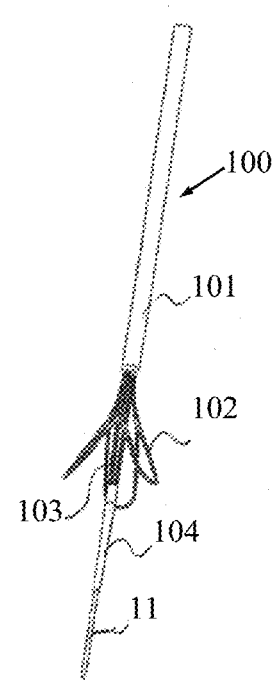
Figure 16D:
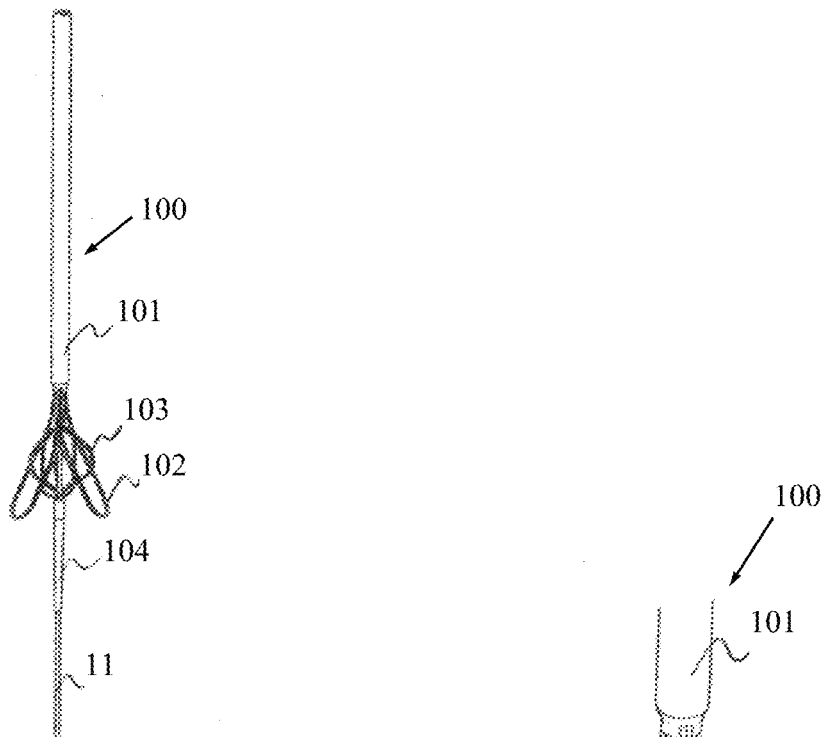

Reference is now made to FIGS. 16A-16D, which illustrate an impactor device 100, in accordance with another non-limiting embodiment of the present invention. Device 100 includes an outer sheath 101 in which are disposed one or more locating elements 102 and one or more (radially) vibratory (impacting) elements 103. Device 100 has a tip 104 which allows it to be guided through the vasculature over guidewire 11. FIGS. 16A through 16D show the gradual withdrawal of outer sheath 101 and the opening of the locating elements 102. FIG. 16D shows the radial opening of vibratory elements 103.

The vibratory mechanism is an active device which can be made to move in-and-out in the radial direction with a frequency and amplitude that is determined by the operator, or comes preset by the manufacturer. The inner vibratory mechanism proceeds to vibrate against the inside of the native leaflet, applying force at a specified location, while the locating elements having been positioned earlier, and provide resistance to said force. The resulting action can remodel the calcification structure within the leaflet.

The vibratory mechanism can be constructed as a tube having slits cut axially around its circumference. Should the tube be compressed such that its ends move one towards the other, the material between the circumferentially cut slits would extend radially outward (elements 103).

Figure 17:
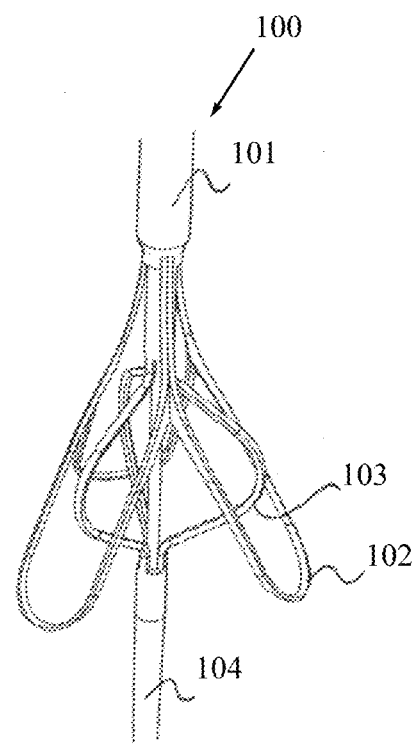
FIG. 17 is a simplified illustration of the distal end of the device of FIGS. 16A-16D, showing locating and vibratory elements in their open positions.

Reference is now made to FIG. 17, which illustrates the distal end of device 100 with both locating and vibratory elements 102 and 103 in their open positions, respectively.

It is noted that vibratory elements 103 may be distributed equally or unequally around the circumference of the device 100.

Figure 18A:
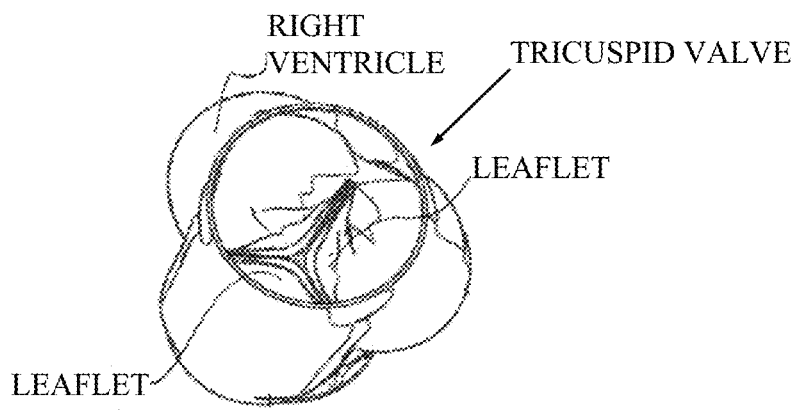
FIGS. 18A and 18B are simplified illustrations of a diseased tricuspid heart valve with diseased leaflets having calcified lesions.
Figure 18B:
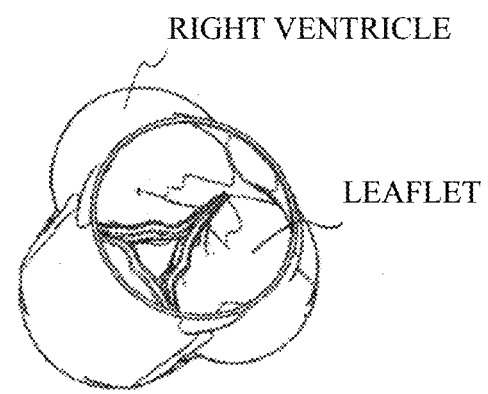
Figure 19A:
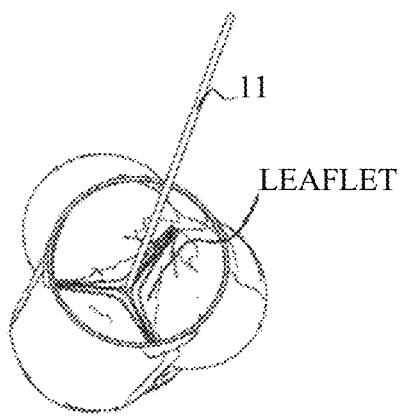
FIGS. 19A-19I are simplified illustrations of a method of using the device of FIGS. 16A-16D, in accordance with another non-limiting embodiment of the present invention.
Figure 19B:
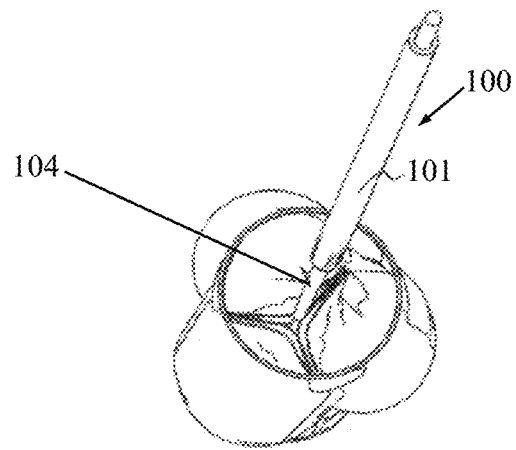
Figure 19C:
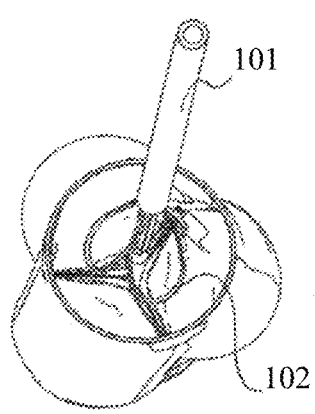
Figure 19D:
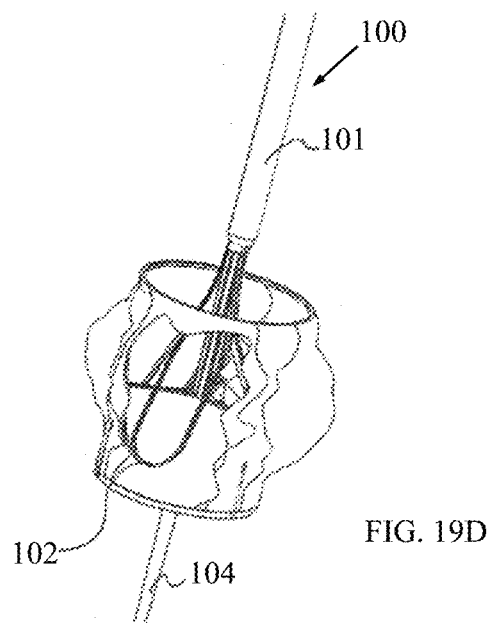
Figure 19E:
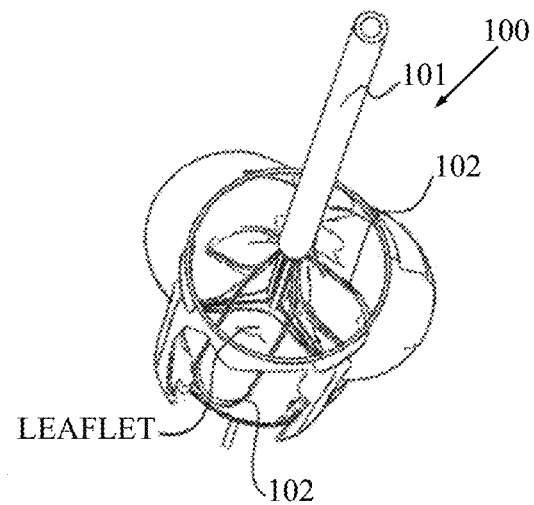
Figure 19F:
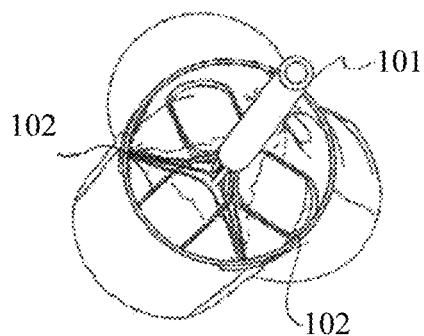
Figure 19G:
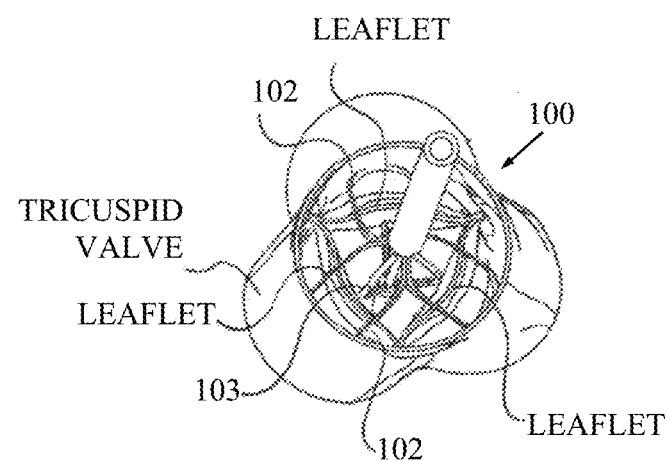
Figure 19H:
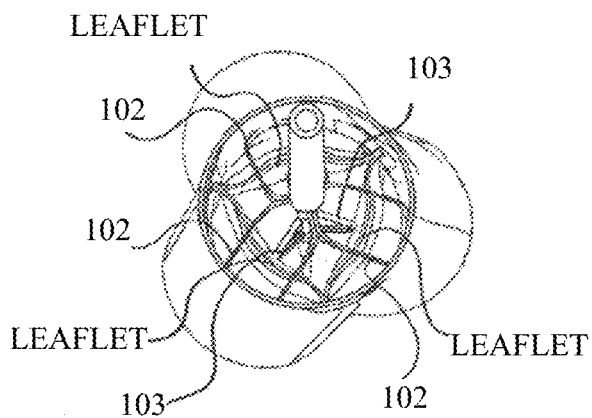
Figure 19I:
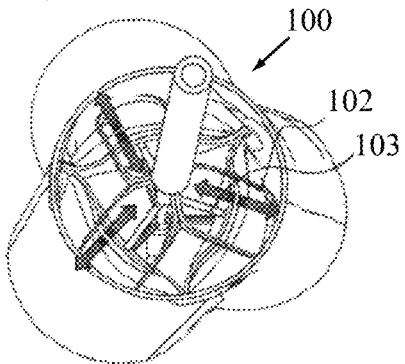

FIGS. 18A and 18B illustrate a diseased tricuspid heart valve with diseased leaflets having calcified lesions. The opening of the valve (FIG. 18B) is adversely affected by the calcification.

Reference is now made to FIGS. 19A-19I, which illustrate the treatment of the diseased valve using the device. Guidewire 11 is introduced into the artery and advanced until its distal end passes through the valve leaflets. In the case of the aortic valve, the guidewire 11 would be advanced until its distal end is located within the left ventricle. The device 100 is advanced over the guidewire 11 until its distal end is located at or near the valve annulus. Outer sheath 101 is withdrawn partially, exposing the locating mechanism whose elements 102 extend radially outward. The device 100 is moved in a distal direction (towards the left ventricle in the case of the aortic valve) so that locating elements 102 rest against the pocket between the downstream surface of the leaflets and the arterial wall. The device 100 can be rotated gently in order to facilitate the proper positioning of the elements 102.

Once in place, the vibrating mechanism is actively expanded radially so that vibratory elements 103 rest against the inside or upstream surface of the valve leaflets. Pretensioning the vibrating elements 103 against the leaflets is possible, such that tension is maintained against the leaflet tissue which is sandwiched between the locating elements 102 and the vibrating elements 103.

The operator can now begin the vibratory motion of elements 103 so that a repetitive force is applied to the inner surface of the leaflets, thus affecting a change in the structure of the calcific buildup within the leaflet tissue.

Figure 20:
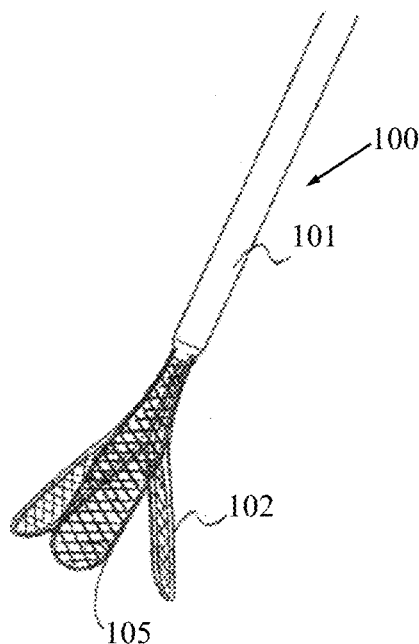
FIG. 20 is a simplified illustration of the locating elements of the device having a mesh connected to them so as to capture any debris that may be created as part of the process.

Reference is now made to FIG. 20, which illustrates the locating elements 102 having a mesh 105 connected to them so as to capture any debris that may be created as part of the process. The mesh can be distributed around the locating elements 102, and can be made out of a wide range of suitable materials.

Figure 21A:
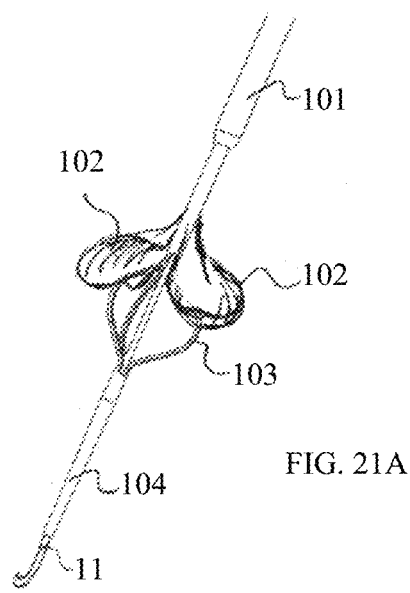
FIGS. 21A and 21B are simplified illustrations of another embodiment wherein the locating elements are inflatable cushions or balloons.
Figure 21B:
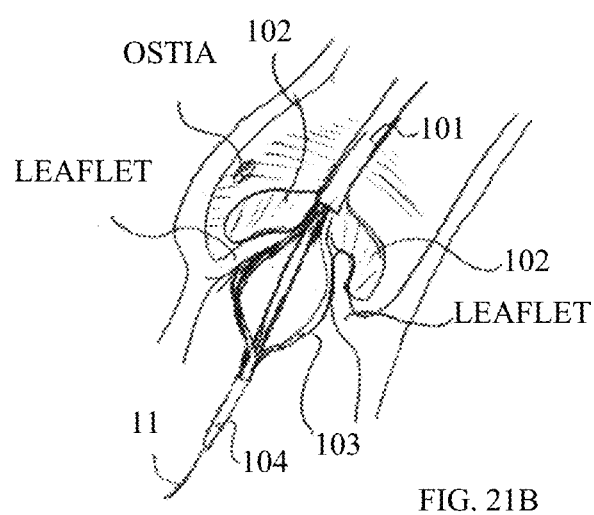

Reference is now made to FIGS. 21A and 21B, which illustrate another possible embodiment wherein the locating elements 102 are inflatable cushions or balloons. The balloons are often filled with a liquid such as saline, and can offer the counter force needed in order to resist the force generated by the vibratory mechanism. The balloons are inflated in such a way as not to block the coronary ostia.

Figure 22A:
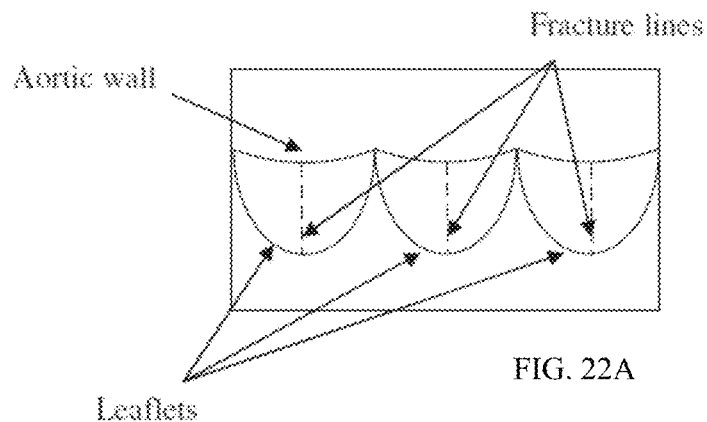
FIG. 22A illustrates a longitudinal cut through the aortic wall with fracture lines created at the centerline of the leaflet by an impactor.
Figure 22B:
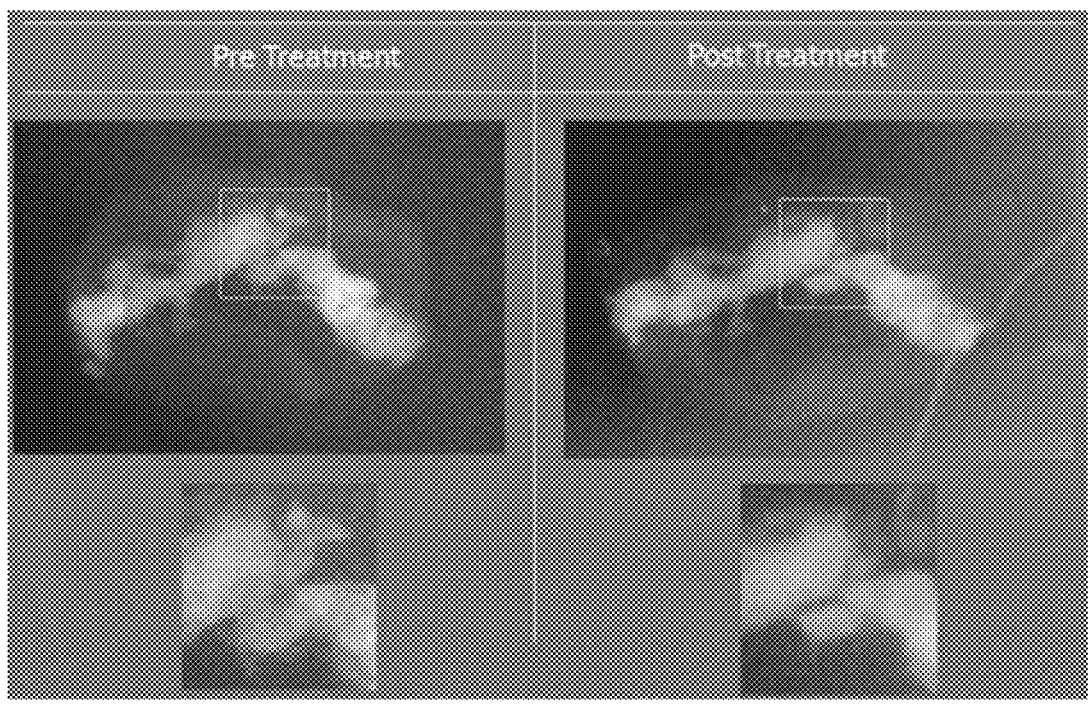
FIG. 22B is an x-ray of a typical leaflet after a single fracture was created close to its centerline.

FIG. 22A illustrates a longitudinal cut through the aortic wall with fracture lines created at the centerline of each leaflet by an impactor (which, for example, has three impacting arms). Similarly any number and pattern of fractures can be pre-set or achieved. FIG. 22B is an x-ray of a typical leaflet after a single fracture was created close to its centerline.

The scope of the present invention includes both combinations and subcombinations of the features described hereinabove as well as modifications and variations thereof which would occur to a person of skill in the art upon reading the foregoing description and which are not in the prior art.

What is claimed is:
1. A method for heart valve treatment comprising:
   providing a first heart valve treatment member movable along a first shaft portion and comprising at least one expandable, non-inflatable member;

providing a second heart valve treatment member movable along a second shaft portion and comprising at least one expandable, non-inflatable member; and wherein said first and second heart valve treatment members are movable between first and second structural positions along said first and second shaft portions, respectively; and in the first structural portion, causing said first heart valve treatment member to be positioned on a proximal side of a heart valve leaflet and causing said second heart valve treatment member to be positioned on a distal side of the heart valve leaflet, and wherein there is a first gap between said first and second heart valve treatment members, said first gap being sized such that none of said first and second heart valve treatment members fractures a portion of the heart valve leaflet, and in the second structural position, causing said at least one expandable, non-inflatable member of said first heart valve treatment member to be in a first expanded shape in which it extends outwards from said first shaft portion at an acute angle with respect to said first shaft portion, and said at least one expandable, non-inflatable member of said second heart valve treatment member to be in a second expanded shape in which a portion of said second heart valve treatment member extends outwards from said second shaft portion at an obtuse angle relative to said acute angle, such that there is a second gap between said first and second heart valve treatment members, said second gap being smaller than said first gap and said second gap being sized such that both of said first and second heart valve treatment members contact the heart valve leaflet and said first heart valve treatment member comprises a fracture edge located on an outer surface thereof directed at said acute angle towards the heart valve leaflet; and fracturing a portion of the heart valve leaflet by axial movement of said first heart valve treatment member, with said fracture edge remaining at said acute angle, towards said second heart valve treatment member which remains expanded at said obtuse angle.

2. The method according to claim 1, wherein said fracture edge pulverizes the portion of the heart valve leaflet.

3. The method according to claim 1, wherein said fracture edge breaks the portion of the heart valve leaflet.

4. The method according to claim 1, wherein said fracture edge grinds the portion of the heart valve leaflet.

5. The method according to claim 1, wherein said fracture edge chops the portion of the heart valve leaflet.

6. The method according to claim 1, wherein said fracture edge cuts the portion of the heart valve leaflet.

7. A heart valve treatment device comprising:
a first heart valve treatment member movable along a first shaft portion and comprising at least one expandable, non-inflatable member;
a second heart valve treatment member movable along a second shaft portion and comprising at least one expandable, non-inflatable member; and
wherein said first and second heart valve treatment members are movable between first and second structural positions along said first and second shaft portions, respectively;

wherein in the first structural position, said first heart valve treatment member is positioned on a proximal side of a heart valve leaflet and said second heart valve treatment member is positioned on a distal side of the heart valve leaflet, and wherein there is a first gap between said first and second heart valve treatment members, said first gap being sized such that none of said first and second heart valve treatment members fractures a portion of the heart valve leaflet, and in the second structural position, said at least one expandable, non-inflatable member of said first heart valve treatment member is in a first expanded shape in which it extends outwards from said first shaft portion at an acute angle with respect to said first shaft portion, and said at least one expandable, non-inflatable member of said second heart valve treatment member is in a second expanded shape in which a portion of said second heart valve treatment member extends outwards from said second shaft portion at an obtuse angle relative to said acute angle, and here is a second gap between said first and second heart valve treatment members, said second gap being smaller than said first gap and said second gap being sized such that both of said first and second heart valve treatment members contact the heart valve leaflet and said first heart valve treatment members comprises a fracture edge located on an outer surface thereof directed at said acute angle towards the heart valve leaflet which is configured to fracture a portion of the heart valve leaflet by axial movement of said first heart valve treatment member, with said fracture edge remaining at said acute angle, towards said second heart valve treatment member which remains expanded at said obtuse angle.

8. The device according to claim 7, wherein said at least one expandable member of said first heart valve treatment member is lockable in said second expanded shape.

9. The device according to claim 7, wherein said first heart valve treatment member comprises a cover.

10. The device according to claim 7, wherein said at least one expandable, non-inflatable member of said first heart valve treatment member comprises at least two arms circumferentially separated from each other about said first shaft, each of said arms having a base coupled to said first shaft and an end opposite said base, wherein in said first expanded shape said ends of each of said arms are radially distanced from said first shaft and said bases remain coupled to said first shaft.

11. The device according to claim 7, wherein said fracture edge comprises a pulverizing edge.

12. The device according to claim 7, wherein said fracture edge comprises a breaking edge.

13. The device according to claim 7, wherein said fracture edge comprises a grinding edge.

14. The device according to claim 7, wherein said fracture edge comprises a chopping edge.

15. The device according to claim 7, wherein said fracture edge comprises a cutting edge.

* * * * *